United States Patent
Zhao (10) Patent No.: US 10,898,372 B2
(45) Date of Patent: Jan. 26, 2021

(54) BOARD-LIKE FORCEPS FOR OPHTHALMIC USE

(71) Applicant: SHENZHEN AIREN MEDICAL GROUP CO. LTD. BEIJING BRANCH, Beijing (CN)

(72) Inventor: Yang Zhao, Beijing (CN)

(73) Assignee: SHENZHEN AIREN MEDICAL GROUP CO. LTD. BEIJING BRANCH, Beijing (CN)

( * ) Notice: Subject to any disclaimer, the term of this patent is extended or adjusted under 35 U.S.C. 154(b) by 147 days.

(21) Appl. No.: 16/302,191

(22) PCT Filed: Apr. 5, 2017

(86) PCT No.: PCT/CN2017/079485
§ 371 (c)(1),
(2) Date: Nov. 16, 2018

(87) PCT Pub. No.: WO2017/197994
PCT Pub. Date: Nov. 23, 2017

(65) Prior Publication Data
US 2019/0209370 A1    Jul. 11, 2019

(30) Foreign Application Priority Data

May 19, 2016 (CN) ..................... 2016 2 0468200 U
Mar. 31, 2017 (CN) .......................... 2017 1 0209985

(51) Int. Cl.
*A61F 9/007* (2006.01)
*A61B 17/30* (2006.01)
*A61B 17/285* (2006.01)
*A61B 17/32* (2006.01)

(52) U.S. Cl.
CPC ............ *A61F 9/007* (2013.01); *A61B 17/285* (2013.01); *A61B 17/30* (2013.01); *A61B 2017/320008* (2013.01); *A61F 9/00709* (2013.01)

(58) Field of Classification Search
CPC ....... A61F 9/007; A61B 17/30; A61B 17/285; A61B 17/282; A61B 17/2841
See application file for complete search history.

(56) References Cited

U.S. PATENT DOCUMENTS

| 4,844,065 A * | 7/1989 | Faulkner ................ A61B 17/30 606/107 |
| 5,147,369 A * | 9/1992 | Wagner .................. A61B 17/30 294/99.2 |
| 2012/0303045 A1* | 11/2012 | Cooper .................. A61B 17/30 606/131 |

* cited by examiner

*Primary Examiner* — Tuan V Nguyen
(74) *Attorney, Agent, or Firm* — Li & Cai Intellectual Property (USA) Office (57) ABSTRACT

Board-like forceps for ophthalmic use comprise forceps handles and forceps boards. The forceps handles comprise an upper forceps handle (1) and a lower forceps handle (2), two ends of which are connected to form a V-type structure. The length of the lower forceps handle (2) is greater than that of the upper forceps handle (1). An upper forceps board (3) and a lower forceps board (4) having a same shape are correspondingly disposed on unconnected ends of the upper forceps handle (1) and the lower forceps handle (2), and are bent in a same side direction. An included angle formed by the upper forceps board (3) and the upper forceps handle (1) is smaller than an included angle formed by the lower forceps board (4) and the lower forceps handle (2).

14 Claims, 11 Drawing Sheets

BOARD-LIKE FORCEPS FOR OPHTHALMIC USE

BACKGROUND OF THE INVENTION

1. Field of the Invention

The present invention relates to a medical instrument, and in particular, to board-like forceps for ophthalmic use.

2. Description of Related Art

Pterygium is a common and frequently-occurring disease in ophthalmology, and refers to an abnormal tissue growth over the cornea in Traditional Chinese medicine, commonly known as "fish-flesh like sarcoma". This eye disease is commonly considered to a chronic inflammatory disease caused by an external stimulus in one eye or both eyes. It gets its name because its shape resembles an insect's wing. As an abnormal superfluous tissue occurring on the bulbar conjunctiva in the palpebral fissure and the cornea, the pterygium encroaches on the cornea and gradually grows, and even can cover the pupil area, thus seriously affecting vision. This abnormal tissue grows into the cornea after degeneration, hypertrophy, and hyperplasia on and beneath the bulbar conjunctiva in the palpebral fissure. To prevent the pterygium from affecting vision of a patient, the best treatment at present is pterygium resection. After surgical removal of the pterygium, it is required to move a conjunctiva graft (which is a membranous tissue on the surface of the eyeball) from another part, so as to perform suturing to cover an exposed wound surface left after cutting. A doctor directly cuts off the graft with scissors, which is the commonly used method at present. However, this method slows down the procedure of the operation, and moreover, it is difficult to manually acquire regular grafts and standardize their sizes. Even if some assistive devices are used to assist the doctor in acquiring the conjunctiva graft, the medical worker still needs to simultaneously operate the assistive devices and the surgical equipment with both hands during the operation. Thus, it is rather inconvenient to perform the operation in the actual process, and the medical worker is under high stress through the whole process, easily incurring an unnecessary injury to the patient.

SUMMARY OF THE INVENTION

Disclosure of the Present Invention

Technical Problem

Because the current pterygium resection totally depends on a bimanual operation of a doctor to cut off the graft with surgical scissors, the doctor is under high stress and an unnecessary injury is easily caused to the patient. To solve this problem, the present invention provides board-like forceps for ophthalmic use, and specific solutions are as follows:

Solutions to the Problem

Technical Solutions

Board-like forceps for ophthalmic use include forceps handles and forceps boards. The forceps handles include an upper forceps handle and a lower forceps handle, wherein one end of the upper forceps handle and one end of the lower forceps handle are fixedly connected, and the other end of each of them freely extends to form an included angle; the length of the lower forceps handle is greater than that of the upper forceps handle; and an upper forceps board and a lower forceps board having a same shape are correspondingly disposed on unconnected ends of the upper forceps handle and the lower forceps handle, and are bent in a same side direction.

Further, an included angle formed by the upper forceps board and the upper forceps handle is unequal to an included angle formed by the lower forceps board and the lower forceps handle, such that the forceps boards can be tightly closed during use, and a doctor can conveniently cut off a graft along the edge of the forceps boards.

Further, the included angle formed by the upper forceps board and the upper forceps handle is smaller than the included angle formed by the lower forceps board and the lower forceps handle.

Further, board surfaces of the forceps boards are both cambered surfaces matching the shape of the eyeball, which is more beneficial to a procedure of an operation performed by the doctor.

Further, skid-proof stripes are formed on the forceps handles, so that the doctor can steadily operate the forceps in the procedure of the operation.

Further, the upper forceps board is smaller than the lower forceps board in size, so that the doctor can cut off the graft along the edge of the upper forceps board with a scalpel.

Further, a blade passage slot is opened on the lower forceps board along the edge of the upper forceps board, so that the doctor can more efficiently and conveniently cut off the graft with the scalpel.

Further, several toothlike notches are opened on the upper forceps board, so that the doctor can conveniently take out the graft clamped between the forceps boards.

Further, a first blade is disposed along an outside edge of a bottom surface of the upper forceps board, and is perpendicular to a plane in which the upper forceps board is located.

Further, a groove corresponding to the first blade is opened on the lower forceps board, wherein the width of the groove is 3 to 5 times greater than the thickness of the first blade, to ensure the width for blade passage, so that a tearing injury is avoided to the conjunctivas around an operative site in the procedure of the operation.

Further, a blade storage cylinder is disposed around the outside edge of the upper forceps board, wherein an inner wall of the blade storage cylinder contacts the first blade, and a cylinder wall thereof is perpendicular to the plane in which the upper forceps board is located; a channel is opened at a position corresponding to the upper forceps handle on the cylinder wall of the blade storage cylinder, and is arranged along the axial direction of the blade storage cylinder; and a resilient spring is disposed between an upper surface of the upper forceps board and an upper edge of the blade storage cylinder. Thus, the first blade resides in the blade storage cylinder when it is not in use, avoiding damage to the blade due to bumping; and during use, as the first blade is moved downwards, the blade storage cylinder can press against the bulbar conjunctiva on the operative site under the effect of the resilient spring, so that the bulbar conjunctiva on the operative site is tightly pressed to avoid an injury to other parts.

Further, a lower edge of the blade storage cylinder is curved outwards to form a press ring which enables the blade storage cylinder to press against the bulbar conjunctiva.

Further, the lower forceps board is provided with a second blade arranged along an outside edge of the lower forceps board, and the second blade and the lower forceps board are located in the same plane, so that the lower forceps board can be directly inserted into the bulbar conjunctiva, simplifying the procedure of the operation.

Further, several via holes are opened on the upper forceps board, through which a conjunctiva graft cut off by using the upper forceps board can be conveniently taken out after the operation.

Beneficial Effects of the Present Invention

Beneficial Effects

The beneficial effects of the present invention are as follows: The present invention provides board-like forceps for ophthalmic use. A conjunctiva graft to be taken can be clamped by using the forceps boards that are arranged in the upper-lower structure, and then a person performing an operation can take out the graft according to the size of the upper forceps board by using scissors or a scalpel, so as to perform suturing to cover an exposed wound surface left after cutting. Thus, the procedure of the operation is simplified, the time is shorter, and the grafts taken out have standard sizes, which better facilitates the postoperative recovery of a patient. Preferably, the lower forceps board with a horizontal blade is inserted into the bulbar conjunctiva to an appropriate depth, and then the upper forceps board with a vertical blade is operated to directly cut off the conjunctiva graft of an appropriate size, so that the person performing the operation can finish taking the conjunctiva graft with only one hand, further simplifying the procedure of the operation.

DESCRIPTION OF REFERENCE NUMERALS IN THE DRAWINGS

1. Upper forceps handle, 2. Lower forceps handle, 3. Upper forceps board, 4. Lower forceps board, 5. Skid-proof stripes, 6. Blade passage slot, 7. First blade, 8. Via holes, 9. Groove, 10. Second blade, 11. Blade storage cylinder, 12. Resilient spring, and 13. Press ring.

DETAILED DESCRIPTION OF THE PREFERRED EMBODIMENTS

Implementations of the Present Invention

In order to explain in detail the technical contents, structural features, objects and effects of the present invention, the embodiments are described below in detail with reference to the accompanying drawings.

Embodiment 1

Figure 1:
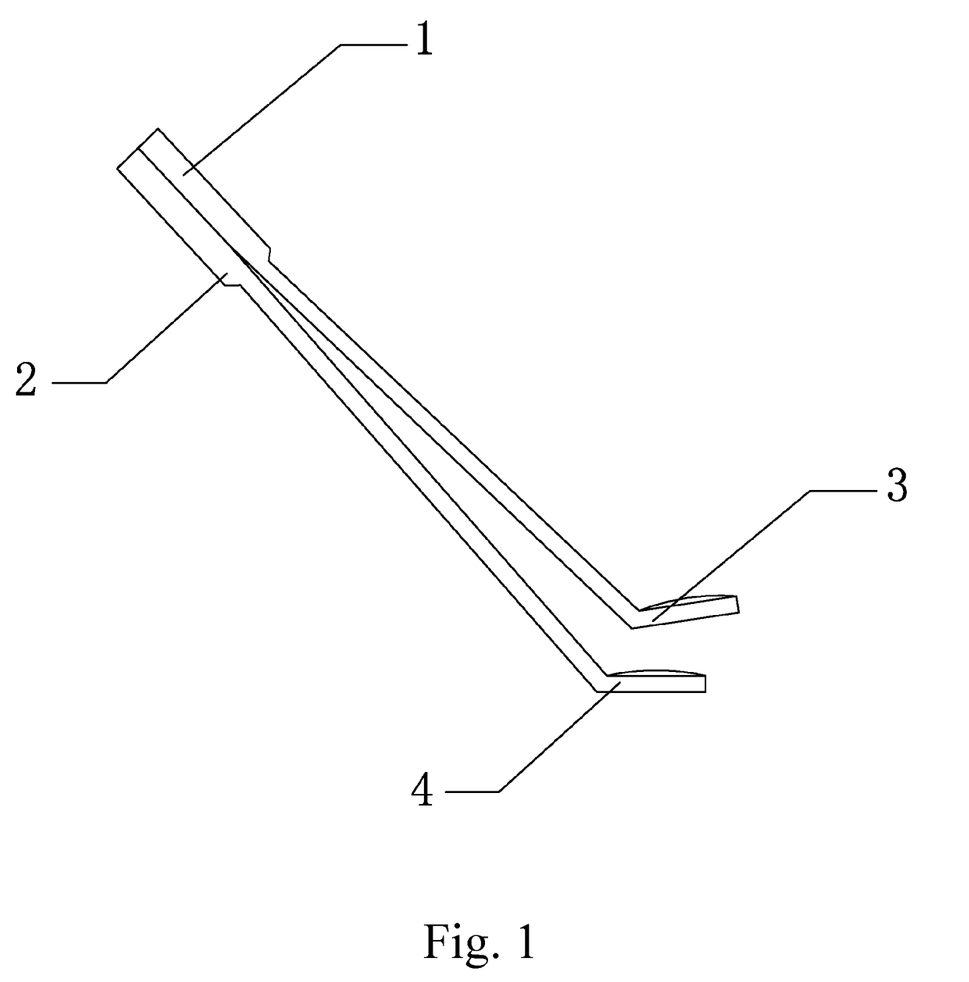
FIG. 1 is a structural side view of Embodiment 1 of the present invention.
Figure 2:
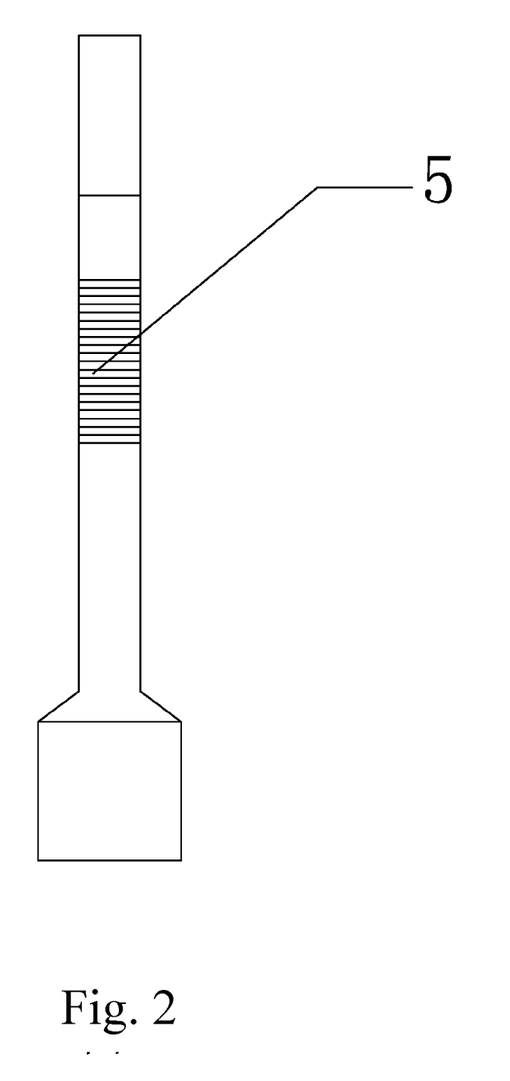
FIG. 2 is a structural top view of Embodiment 1 of the present invention.

As shown in FIG. 1 and FIG. 2, board-like forceps for ophthalmic use include forceps handles and forceps boards. The forceps handles include an upper forceps handle 1 and a lower forceps handle 2, wherein one end of the upper forceps handle and one end of the lower forceps handle are fixedly connected, and the other end of each of them freely extends to form an included angle. The length of the lower forceps handle 2 is greater than that of the upper forceps handle 1. An upper forceps board 3 and a lower forceps board 4 having a same shape are correspondingly disposed on unconnected ends of the upper forceps handle 1 and the lower forceps handle 2, and are bent in a same side direction. An included angle formed by the upper forceps board 3 and the upper forceps handle 1 is unequal to an included angle formed by the lower forceps board 4 and the lower forceps handle 2, such that the forceps boards can be tightly closed during use. Board surfaces of the forceps boards are both cambered surfaces matching the shape of the eyeball, which is more beneficial to the procedure of an operation performed by a doctor. Skid-proof stripes 5 are formed on the forceps handles, so that the doctor can steadily operate the forceps in the procedure of the operation.

After surgical removal of pterygium, the doctor needs to move a conjunctiva graft from another part, so as to perform suturing to cover an exposed wound surface left after cutting. In this case, the doctor can use the forceps to clamp a slice of conjunctiva graft of a specified size, and then cut off the conjunctiva graft along the edge of the forceps boards with surgical scissors, to use it in the subsequent suturing step.

Embodiment 2

Figure 3:
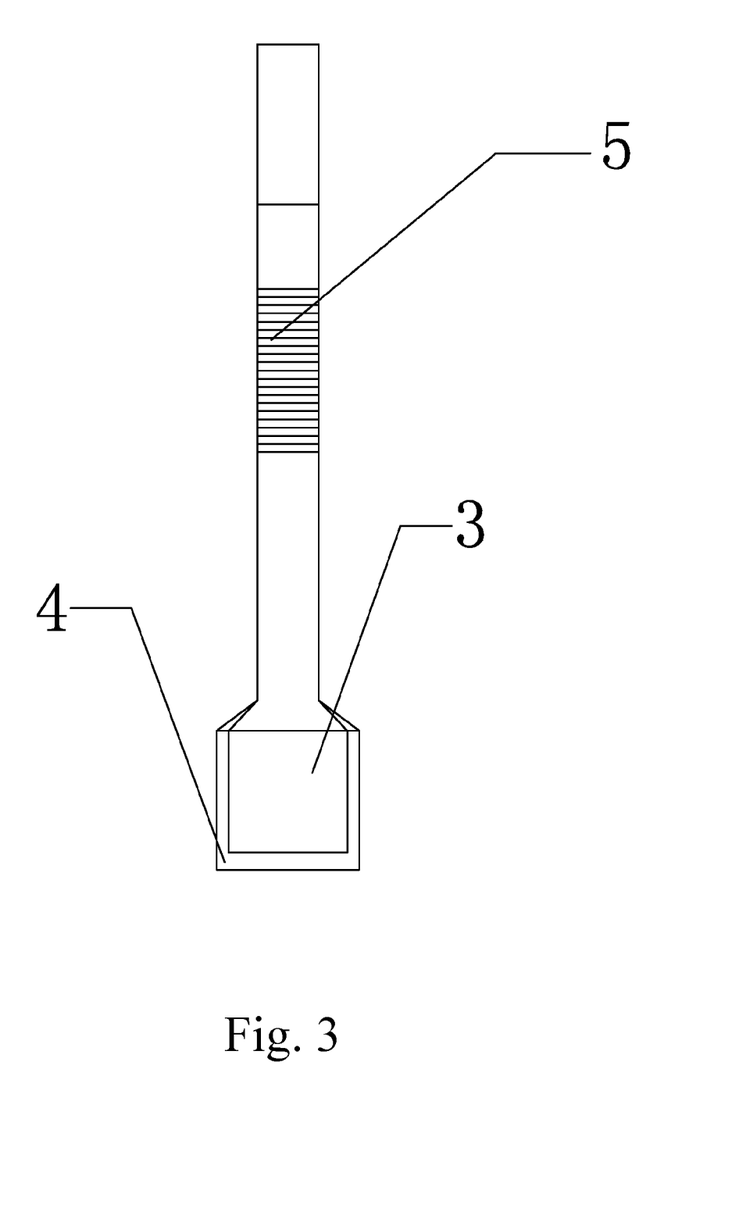
FIG. 3 is a structural top view of Embodiment 2 of the present invention.

As shown in FIG. 1 and FIG. 3, board-like forceps for ophthalmic use include forceps handles and forceps boards. The forceps handles include an upper forceps handle 1 and a lower forceps handle 2, wherein one end of the upper forceps handle and one end of the lower forceps handle are fixedly connected, and the other end of each of them freely extends to form an included angle. The length of the lower forceps handle 2 is greater than that of the upper forceps handle 1. An upper forceps board 3 and a lower forceps board 4 are correspondingly disposed on unconnected ends of the upper forceps handle 1 and the lower forceps handle 2. The upper forceps board 3 is smaller than the lower forceps board 4 in size, and the upper forceps board 3 and the lower forceps board 4 are bent in a same side direction. An included angle formed by the upper forceps board 3 and the upper forceps handle 1 is unequal to an included angle formed by the lower forceps board 4 and the lower forceps handle 2, such that the forceps boards can be tightly closed during use. Board surfaces of the forceps boards are both cambered surfaces matching the shape of the eyeball, which is more beneficial to the procedure of an operation performed by a doctor. Skid-proof stripes 5 are formed on the forceps handles, so that the doctor can steadily operate the forceps in the procedure of the operation.

After surgical removal of pterygium, the doctor needs to move a conjunctiva graft from another part, so as to perform suturing to cover an exposed wound surface left after cutting. In this case, the doctor can use the forceps to clamp a slice of conjunctiva graft of a specified size, and then cut off the conjunctiva graft along the edge of the upper forceps board with a scalpel, to use it in the subsequent suturing step.

Embodiment 3

Figure 4:
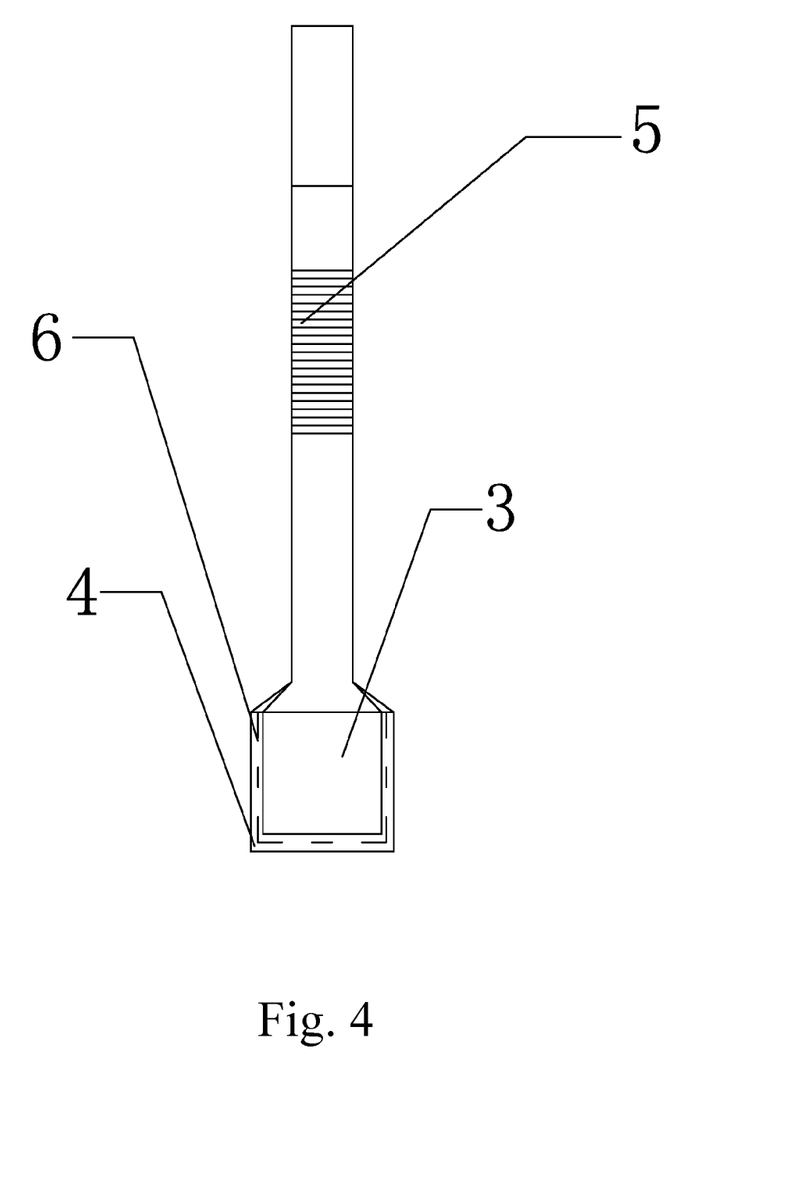
FIG. 4 is a structural top view of Embodiment 3 of the present invention.

As shown in FIG. 1 and FIG. 4, board-like forceps for ophthalmic use include forceps handles and forceps boards. The forceps handles include an upper forceps handle 1 and a lower forceps handle 2, wherein one end of the upper forceps handle and one end of the lower forceps handle are fixedly connected, and the other end of each of them freely extends to form an included angle. The length of the lower forceps handle 2 is greater than that of the upper forceps handle 1. An upper forceps board 3 and a lower forceps board 4 are correspondingly disposed on unconnected ends of the upper forceps handle 1 and the lower forceps handle 2. The lower forceps board 4 is larger than the upper forceps board 3 in size, and a blade passage slot 6 is opened on the lower forceps board 4 along the edge of the upper forceps board 3. The upper forceps board 3 and the lower forceps board 4 are bent in a same side direction. An included angle formed by the upper forceps board 3 and the upper forceps handle 1 is unequal to an included angle formed by the lower forceps board 4 and the lower forceps handle 2, such that the forceps boards can be tightly closed during use. Board surfaces of the forceps boards are both cambered surfaces matching the shape of the eyeball, which is more beneficial to the procedure of an operation performed by a doctor. Skid-proof stripes 5 are formed on the forceps handles, so that the doctor can steadily operate the forceps in the procedure of the operation.

After surgical removal of pterygium, the doctor needs to move a conjunctiva graft from another part, so as to perform suturing to cover an exposed wound surface left after cutting. In this case, the doctor can use the forceps to clamp a slice of conjunctiva graft of a specified size, and then cut off the conjunctiva graft along the blade passage slot opened on the lower forceps board with a scalpel, to use it in the subsequent suturing step.

Embodiment 4

Figure 5:
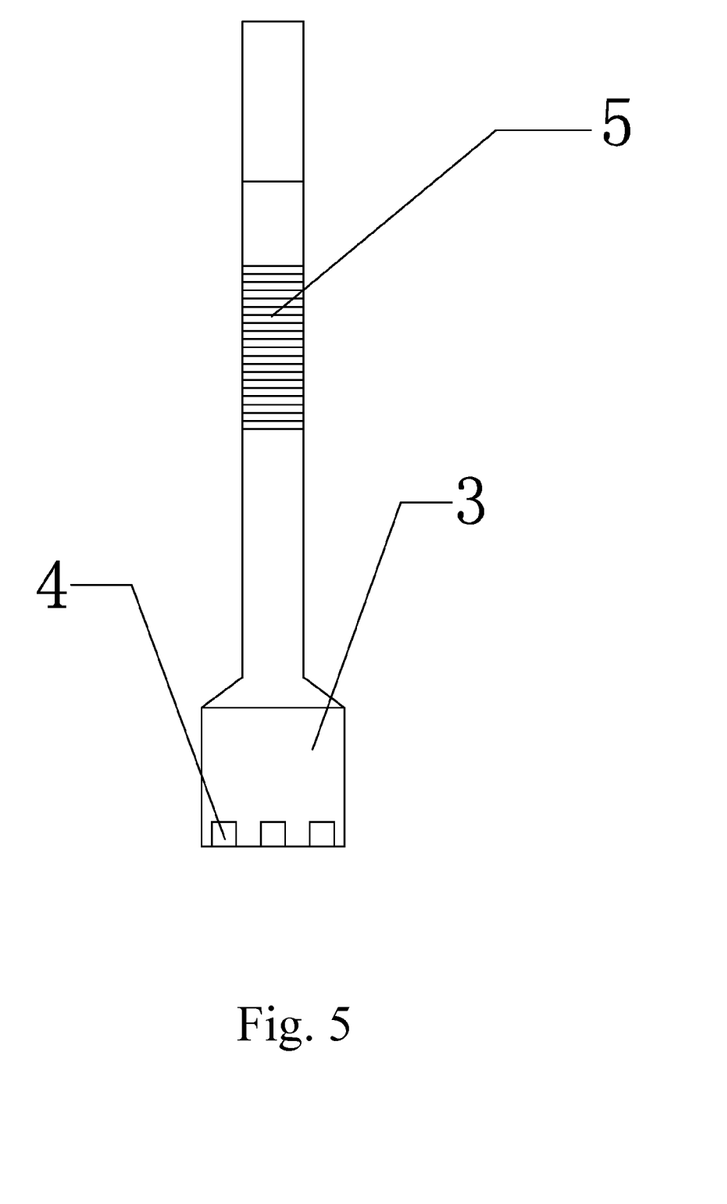
FIG. 5 is a structural top view of Embodiment 4 of the present invention.

As shown in FIG. 1 and FIG. 5, board-like forceps for ophthalmic use include forceps handles and forceps boards. The forceps handles include an upper forceps handle 1 and a lower forceps handle 2, wherein one end of the upper forceps handle and one end of the lower forceps handle are fixedly connected, and the other end of each of them freely extends to form an included angle. The length of the lower forceps handle 2 is greater than that of the upper forceps handle 1. An upper forceps board 3 and a lower forceps board 4 having the same size are correspondingly disposed on unconnected ends of the upper forceps handle 1 and the lower forceps handle 2. Several toothlike notches are opened on the upper forceps board 3, and the upper forceps board 3 and the lower forceps board 4 are bent in a same side direction. An included angle formed by the upper forceps board 3 and the upper forceps handle 1 is unequal to an included angle formed by the lower forceps board 4 and the lower forceps handle 2, such that the forceps boards can be tightly closed during use. Board surfaces of the forceps boards are both cambered surfaces matching the shape of the eyeball, which is more beneficial to the procedure of an operation performed by a doctor. Skid-proof stripes 5 are formed on the forceps handles, so that the doctor can steadily operate the forceps in the procedure of the operation.

After surgical removal of pterygium, the doctor needs to move a conjunctiva graft from another part, so as to perform suturing to cover an exposed wound surface left after cutting. In this case, the doctor can use the forceps to clamp a slice of conjunctiva graft of a specified size, and then cut off the conjunctiva graft along the edge of the forceps boards with surgical scissors. The doctor can easily take out the conjunctiva graft clamped by the lower forceps board through the toothlike notches opened on the upper forceps board, to use it in the subsequent suturing step.

Embodiment 5

Figure 6:
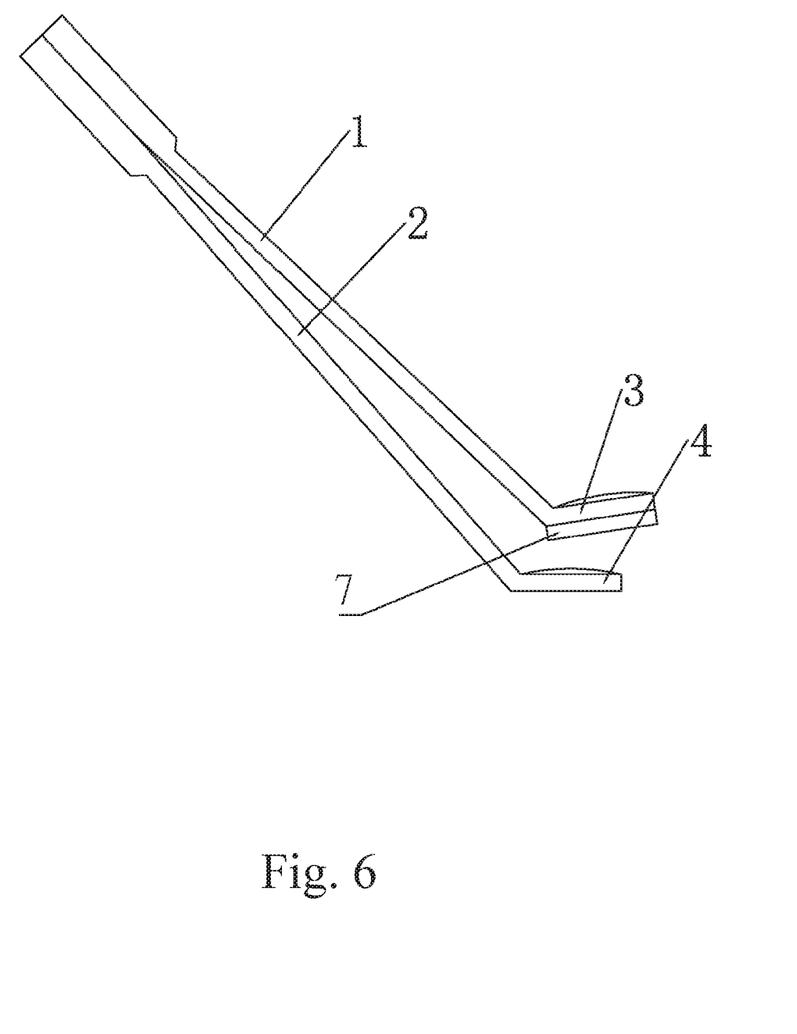
FIG. 6 is a structural side view of Embodiment 5 of the present invention.
Figure 7:
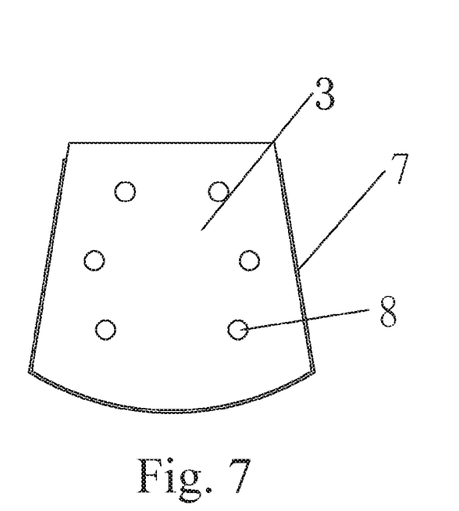
FIG. 7 is a schematic structural diagram of an upper forceps board in Embodiment 5 of the present invention.
Figure 8:
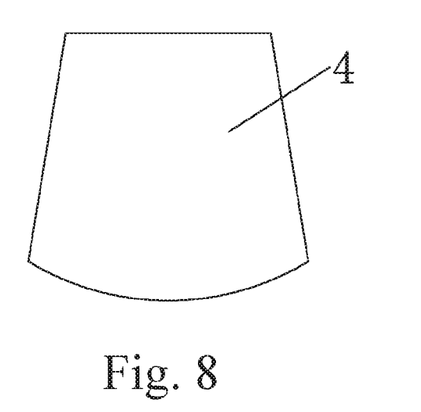
FIG. 8 is a schematic structural diagram of a lower forceps board in Embodiment 5 of the present invention.

As shown in FIG. 6 to FIG. 8, board-like forceps for ophthalmic use include an upper forceps handle 1 and a lower forceps handle 2 fixedly connected on connected ends, wherein an included angle is formed between the upper forceps handle 1 and the lower forceps handle 2. Unconnected ends of the upper forceps handle 1 and the lower forceps handle 2 are both bent upwards to form an upper forceps board 3 and a lower forceps board 4 respectively. The length of the upper forceps handle 1 is less than that of the lower forceps handle 2. An included angle formed by the upper forceps board 3 and the upper forceps handle 1 is less than an included angle formed by the lower forceps board 4 and the lower forceps handle 2. A projected area of the upper forceps board 3 and a projected area of the lower forceps board 4 in the horizontal plane are equal, and thus the upper forceps board 3 completely overlaps the lower forceps board 4 when the upper forceps handle 1 and the lower forceps handle 2 are pinched together. The upper forceps board 3 and the lower forceps board 4 both have a centrally convex cambered surface, and thus they well match the shape of the eyeball, ensuring the operation effect.

As shown in FIG. 6 and FIG. 7, a first blade 7 is disposed along an outside edge of a bottom surface of the upper forceps board 3, and is perpendicular to a plane in which the upper forceps board 3 is located. When the upper forceps handle 1 and the lower forceps handle 2 are pinched together, the first blade 7 can be used to cut off a conjunctiva graft of a specified size. Several via holes 8 are opened on the upper forceps board 3. After the operation, normal saline can be used to flush out the conjunctiva graft cut off by the first blade 7 through these via holes, thus preventing the conjunctiva graft from adhering to the bottom of the upper forceps board 3.

Embodiment 6

Figure 9:
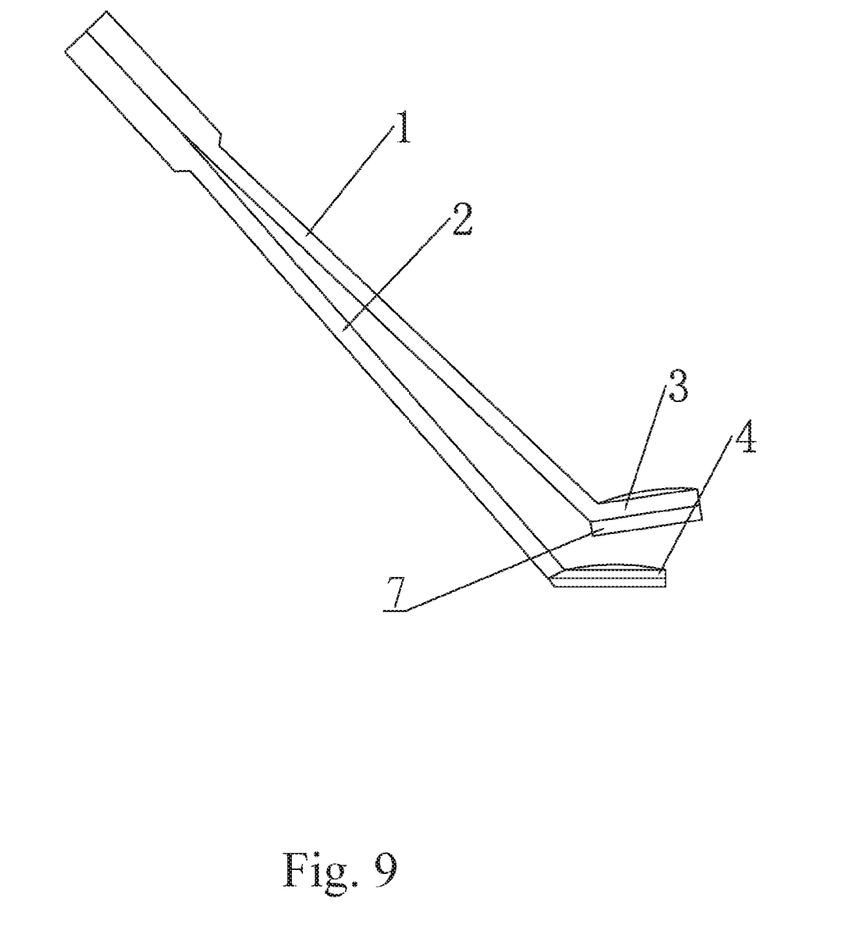
FIG. 9 is a structural side view of Embodiment 6 of the present invention.
Figure 10:
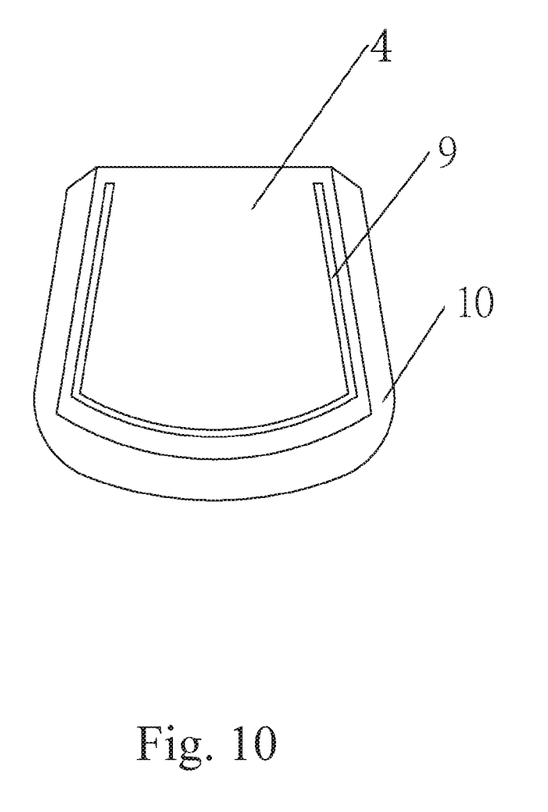
FIG. 10 is a schematic structural diagram of a lower forceps board in Embodiment 6 of the present invention.

With reference to FIG. 9 and FIG. 10 in combination, a difference between Embodiment 6 and Embodiment 5 is as follows: A projected area of the upper forceps board 3 in the horizontal plane is smaller than that of the lower forceps board 4 in the horizontal plane, and a groove 9 corresponding to the first blade 7 is opened on the lower forceps board 4, where the width of the groove 9 is 3 to 5 times greater than the thickness of the first blade 7, to ensure the width for blade passage, so that a tearing injury is avoided to the conjunctivas around an operative site in the procedure of the operation. The lower forceps board 4 is provided with a second blade 10 arranged along an outside edge of the lower forceps board 4, and the second blade 10 and the lower forceps board 4 are located in the same plane, so that the lower forceps board 4 can be directly inserted into the bulbar conjunctiva, simplifying the procedure of the operation.

Embodiment 7

Figure 11:
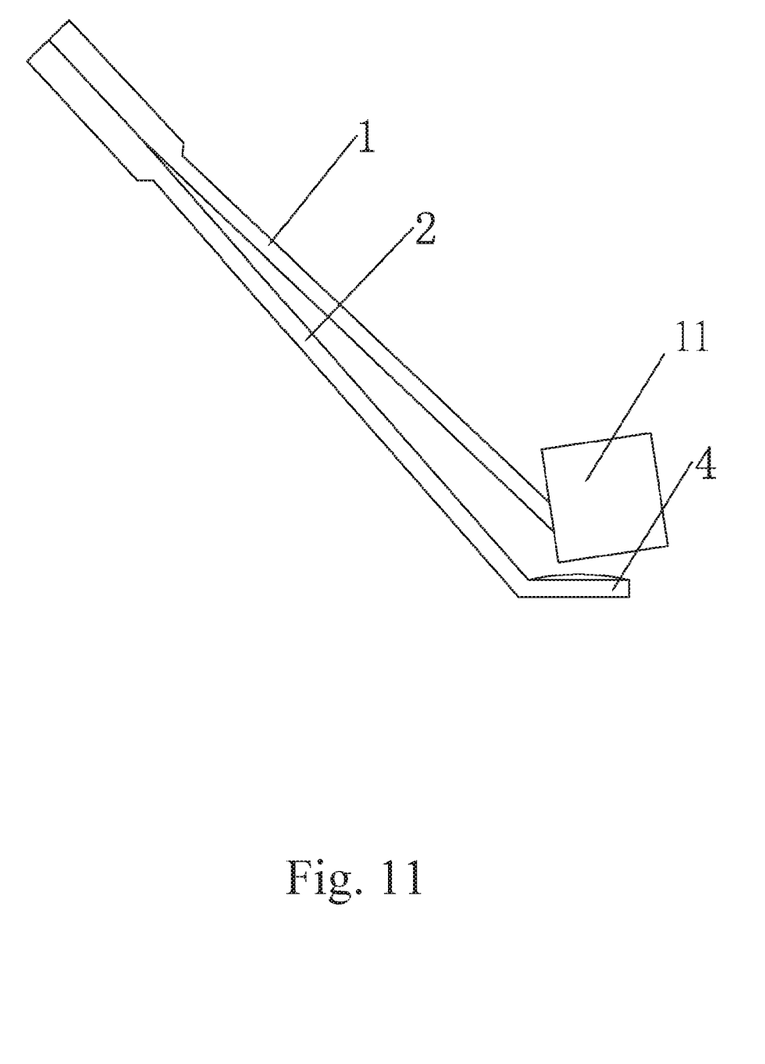
FIG. 11 is a structural side view of Embodiment 7 of the present invention.
Figure 12:
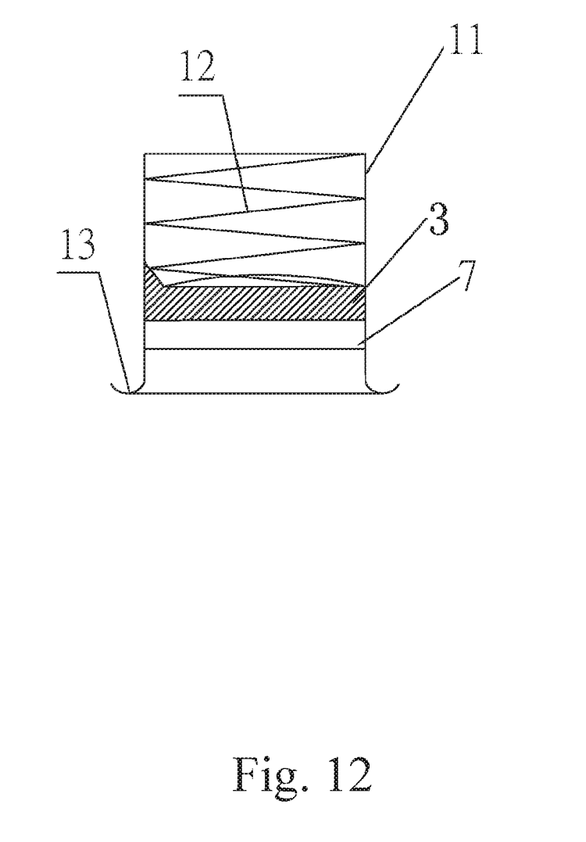
FIG. 12 is a schematic structural diagram of the inside of a blade storage cylinder in Embodiment 7 of the present invention.

With reference to FIG. 11 and FIG. 12, a difference between Embodiment 7 and Embodiment 5 is as follows: A blade storage cylinder 11 is disposed around the outside edge of the upper forceps board 3, wherein an inner wall of the blade storage cylinder 11 contacts the first blade 7, and a cylinder wall thereof is perpendicular to the plane in which the upper forceps board 3 is located. A lower edge of the blade storage cylinder 11 is curved outwards to form a press ring 13 which enables the blade storage cylinder 11 to press against the bulbar conjunctiva. A channel is opened at a position corresponding to the upper forceps handle 1 on the cylinder wall of the blade storage cylinder 11, and is arranged along the axial direction of the blade storage cylinder 11. The upper forceps handle 1 can move inside the channel, such that the upper forceps board can move up and down in the blade storage cylinder. A resilient spring 12 is disposed between an upper surface of the upper forceps board 3 and an upper edge of the blade storage cylinder 11. Thus, the first blade 7 resides in the blade storage cylinder 11 when it is not in use, avoiding damage to the first blade 7 due to bumping. During use, as the first blade 7 is moved downwards, the blade storage cylinder 11 can press against the bulbar conjunctiva on the operative site under the effect of the resilient spring 12, so that the bulbar conjunctiva on the operative site is tightly pressed to avoid an injury to other parts. The first blade 7 is continuously moved downwards till the bulbar conjunctiva on a corresponding position is cut off.

To sum up, the above merely describes preferred embodiments of the present invention, and does not limit the protection scope of the present invention. Equivalent changes and modifications made in accordance with the scope of the present invention and the contents of the specification all fall within the scope of claims of the present invention.

What is claimed is:

1. Board-like forceps for ophthalmic use, comprising forceps handles and forceps boards, wherein the forceps handles comprise an upper forceps handle (1) and a lower forceps handle (2), a proximal end of the upper forceps handle and a proximal end of the lower forceps handle are fixedly connected, and a distal end of each of the lower forceps handle and a distal end of the upper forceps handle freely extends to form an included angle; the length of the lower forceps handle (2) is greater than that of the upper forceps handle (1); and an upper forceps board (3) and a lower forceps board (4) having a same shape are correspondingly disposed on the distal ends of the upper forceps handle (1) and the lower forceps handle (2), and are bent in a same side direction.

2. The board-like forceps for ophthalmic use according to claim 1, wherein an included angle formed by the upper forceps board (3) and the upper forceps handle (1) is unequal to an included angle formed by the lower forceps board (4) and the lower forceps handle (2).

3. The board-like forceps for ophthalmic use according to claim 2, wherein the included angle formed by the upper forceps board (3) and the upper forceps handle (1) is smaller than the included angle formed by the lower forceps board (4) and the lower forceps handle (2).

4. The board-like forceps for ophthalmic use according to claim 1, wherein board surfaces of the forceps boards are both cambered surfaces.

5. The board-like forceps for ophthalmic use according to claim 1, wherein skid-proof stripes are formed on the forceps handles.

6. The board-like forceps for ophthalmic use according to claim 1, wherein the upper forceps board (3) is smaller than the lower forceps board (4) in size.

7. The board-like forceps for ophthalmic use according to claim 5, wherein a blade passage slot is opened on the lower forceps board (4) along the edge of the upper forceps board (3).

8. The board-like forceps for ophthalmic use according to claim 5, wherein several toothlike notches are opened on the upper forceps board (3).

9. The board-like forceps for ophthalmic use according to claim 1, wherein a first blade (5) is disposed along an outside edge of a bottom surface of the upper forceps board (3), and is perpendicular to a plane in which the upper forceps board (3) is located.

10. The board-like forceps for ophthalmic use according to claim 9, wherein a groove (7) corresponding to the first blade (5) is opened on the lower forceps board (4), and the width of the groove (7) is 3 to 5 times greater than the thickness of the first blade (5).

11. The board-like forceps for ophthalmic use according to claim 9, wherein a blade storage cylinder (9) is disposed around the outside edge of the upper forceps board (3), an inner wall of the blade storage cylinder (9) contacts the first blade (5), and a cylinder wall thereof is perpendicular to the plane in which the upper forceps board (3) is located; a channel is opened at a position corresponding to the upper forceps handle (1) on the cylinder wall of the blade storage cylinder (9), and is arranged along the axial direction of the blade storage cylinder (9); and a resilient spring (10) is disposed between an upper surface of the upper forceps board (3) and an upper edge of the blade storage cylinder (9).

12. The board-like forceps for ophthalmic use according to claim 11, wherein a lower edge of the blade storage cylinder (9) is curved outwards to form a press ring (11).

13. The board-like forceps for ophthalmic use according to claim 9, wherein the lower forceps board (4) is provided with a second blade (8) arranged along an outside edge of the lower forceps board (4).

14. The board-like forceps for ophthalmic use according to claim 9, wherein several via holes (6) are opened on the upper forceps board (3).

* * * * *